US 7,635,783 B2

(12) United States Patent
Chevalier et al.

(10) Patent No.: US 7,635,783 B2
(45) Date of Patent: Dec. 22, 2009

(54) MESO-SELECTIVE SYNTHESIS OF ANSA-METALLOCENES

(75) Inventors: Reynald Chevalier, Paris (FR); Patrik Müller, Frankfurt (DE); Christian Sidot, Compiègne (FR); Christian Tellier, Compiègne (FR); Valerie Garcia, Compiègne (FR); Ludovic Delancray, Cuise-la-Motte (FR)

(73) Assignee: Basell Polyolefine GmbH, Wesseling (DE)

( * ) Notice: Subject to any disclaimer, the term of this patent is extended or adjusted under 35 U.S.C. 154(b) by 666 days.

(21) Appl. No.: 10/583,574

(22) PCT Filed: Dec. 15, 2004

(86) PCT No.: PCT/EP2004/014247

§ 371 (c)(1),
(2), (4) Date: Jun. 19, 2006

(87) PCT Pub. No.: WO2005/058929

PCT Pub. Date: Jun. 30, 2005

(65) Prior Publication Data

US 2007/0155920 A1 Jul. 5, 2007

Related U.S. Application Data

(60) Provisional application No. 60/542,579, filed on Feb. 5, 2004.

(30) Foreign Application Priority Data

Dec. 19, 2003 (DE) ................................ 103 60 060

(51) Int. Cl.
*C07F 17/00* (2006.01)
*B01J 31/00* (2006.01)

(52) U.S. Cl. ............................. 556/11; 556/12; 556/43; 556/53; 556/58; 502/103; 502/117; 526/943

(58) Field of Classification Search ................... 556/11, 556/12, 43, 53, 58; 502/103, 117; 526/943
See application file for complete search history.

(56) References Cited

U.S. PATENT DOCUMENTS 6,548,441 B1  4/2003  McDaniel et al.

FOREIGN PATENT DOCUMENTS

| EP | 643078 | 3/1995 |
|---|---|---|
| WO | 2004/037834 | 5/2004 |
| WO | 2004/037840 | 5/2004 |

OTHER PUBLICATIONS

Balboni et al., Inorganic Chemistry, vol. 40, No. 26, pp. 6588-6597 (2001).*
T. Kuhnen et al., "Using Hydrosilylation To Assemble Organometallic Polymers Containing Combinations of Silicon-Based Functional Groups," *Organometallics*, vol. 16(23), pp. 5042-5047 (1997).
A. Bolig et al., "ansa-Zirconocene Ester Enolates: Synthesis, Structure, Reaction with Organo-Lewis Acids, and Application to Polymerization of Methacrylates," *J. Am. Chem. Soc.*, vol. 126(15), pp. 4897-4906 (2004) XP002327853.
D. Balboni et al., "Group 4 Dimethylmetallocenes: Improved Synthesis and Reactivity Studies," *Inorganic Chem.*, vol. 40(26), p. 6588-6597 (2001) XP002327854.
K. Soga et al., "Polymerization of 1-olefins with bulky substituents catalyzed by an optically active metallocene catalyst," *Kobunshi Ronbunshu*, vol. 54(10), pp. 746-748 (1997) XP009047157.
M. Huttenloch et al., "ansa-Metallocene derivatives XXXIX Biphenyl-bridged metallocene complexes of titanium, zirconium, and vanadium: syntheses, crystal structures and enantioseparation," *Journal of Organometallic Chemistry*, vol. 541(1-2), pp. 219-232 (1997) XP004093720.
B. Chin et al., "Improved Procedure for the Preparation of Enantiomerically Pure Ethylenebis(tetrahydroindenyl)zirconium Derivatives," *J. Org. Chem.*, vol. 62(7), pp. 2267-2268 (1997) XP002327855.
W. Kaminsky, Stereospecific oligo- and polymerization with metallocene catalysts,: *Macromol. Symp.*, vol. 89, pp. 203-219 (1995) XP000509167.
W. Kaminsky et al., "Enantioselective Oligomerization of Alpha Olefins with Chiral Zirconocene/Aluminoxane Catalysts," *Organic Synthesis via Organometallics* (OSM 4), Proceedings of the Fourth Symposium in Aachen, Jul. 15-18, 1992, pp. 151-163 (1992) XP009047158.
J. Chien et al., "Difference in stereoselective polymerization of 4-methyl-1-hexene by homogeneous and heterogeneous Ziegler-Natta catalysts," *Makromol. Chem., Rapid Commun.*, vol. 13(11), pp. 479-484 (1992) XP000309571.
W. Kaminsky et al., "Asymmetric Oligomerization of Propene and 1-Butene with a Zirconocene/Alumoxane Catalyst," *Angewandte Chem. Int. Ed.*, vol. 28(9), pp. 1216-1218 (1989) XP002327856.
A. Schaefer et al., "ansa-Metallocene derivatives. XII. Diastereomeric Derivatization and Enantiomer Separation of Ethylenebis(Tetrahydroindenyl)Titanium and Zirconium Dichlorides," *Journal of Organometallic Chem.*, vol. 328(1-2), pp. 87-99 (1987) XP002327857.

* cited by examiner

*Primary Examiner*—Porfirio Nazario Gonzalez
(74) *Attorney, Agent, or Firm*—Connolly Bove Lodge & Hutz, LLP; Jarrod Raphael

(57) ABSTRACT

The present invention relates to a process for the meso-selective preparation of ansa-metallocene complexes of the formula (I), which comprises reacting a ligand starting compound of the formula (II) with a transition metal compound of the formula III, where $R^1$, $R^1$ are identical or different and are each hydrogen or an organic radical having from 1 to 40 carbon atoms, $R^2$, $R^2$ are identical or different and are each hydrogen or an organic radical having from 1 to 40 carbon atoms, $R^3$ is a bulky organic radical which has at least 3 carbon atoms, is bound to the oxygen atom via a nonaromatic carbon or silicon atom and may be substituted by halogen atoms or further organic radicals having from 1 to 20 carbon atoms and may also contain heteroatoms selected from the group consisting of Si, N, P, O and S, T, T' are identical or different and are each a divalent organic group which has from 1 to 40 carbon atoms and together with the cyclopentadienyl ring forms at least one further saturated or unsaturated, substituted or unsubstituted ring system having a ring size of from 5 to 12 atoms, where T and T' may contain the heteroatoms Si, Ge, N, P, As, Sb, O, S, Se or Te within the ring system fused to the cyclopentadienyl ring, A is a bridge consisting of a divalent atom or a divalent group, $M^1$ is an element of group 3, 4, 5 or 6 of the Periodic Table of the Elements or the lanthanides, the radicals X are identical or different and are each an organic or inorganic radical which is able to be replaced by a cyclopentadienyl anion, x is a natural number from 1 to 4, $M^2$ is an alkali metal, an alkaline earth metal or a magnesium monohalide fragment, p is 1 in the case of doubly positively charged metal ions or 2 in the case of singly positively charged metal ions or metal ion fragments, LB is an uncharged Lewis base ligand, and y is a natural number from 0 to 6, and also the subsequent reaction of these complexes to form ansa-metallocenes of the formula (IV), the use of transition metal compounds of the formula (III) for preparing metallocenes and also transition metal compounds of the formula (III), ansa-metallocene complexes of the formula (I) and the use of these as constituents of catalyst systems for the polymerization of olefines.

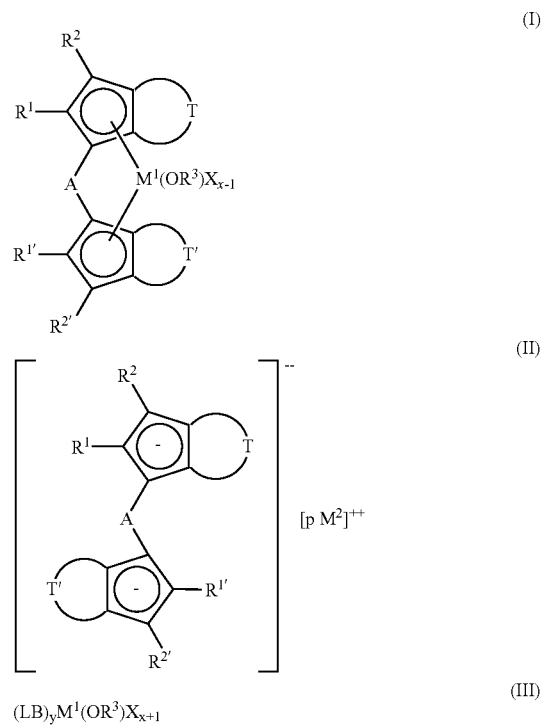

13 Claims, No Drawings

MESO-SELECTIVE SYNTHESIS OF ANSA-METALLOCENES

The present invention relates to a process for the meso-selective preparation of ansa-metallocene complexes of the formula (I), the subsequent reaction of these complexes to form ansa-metallocenes of the formula (I), the use of transition metal compounds of the formula (III) for preparing metallocenes and also transition metal compounds of the formula (III), ansa-metallocene complexes of the formula (I) and the use of these as constituents of catalyst systems for the polymerization of olefins.

Research and development on the use of organic transition metal compounds, in particular metallocenes, as catalyst components for the polymerization and copolymerization of olefins with the objective of preparing tailored polyolefins has been pursued vigorously in universities and in industry over the past 15 years.

Now, not only the ethylene-based polyolefins prepared by means of metallocene catalyst systems and also, in particular, the propylene-based polyolefins prepared by means of metallocene catalyst systems represent a dynamically growing market segment.

To prepare isotactic polypropylenes, ansa-metallocenes in their racemic form are generally used. In the synthesis of the racemic ansa-metallocenes, these are generally obtained together with the undesired meso-metallocenes which are usually separated off without the meso-metallocenes being able to be isolated. It is generally known that ansa-metallocenes in the meso form are responsible for the formation of atactic polypropylenes when used as catalyst constituents.

EP 0 643 078 describes the use of a particular ansa-metallocene in the meso form for preparing very high molecular weight homopolymers and copolymers of ethylene.

While in the case of racemic metallocenes, various racemoselective syntheses have been developed, there has hitherto not yet been an urgent need to develop corresponding meso-selective syntheses.

Organometallics 1997, 16, 5046-49, describes the synthesis of a meso-metallocene or of the corresponding rac-metallocene, in which precisely one of the two possible metallocene forms was formed starting from an isolated diastereomer of a distannylated biscyclopentadienyl ligand system. However, the diastereomerically pure distannylated biscyclopentadienyl ligand system had previously been obtained by separation of the corresponding mixture of diastereomers.

The literature also describes cases in which the rac/meso ratios of the metallocene isomers were dependent on the solvent used in the syntheses starting from zirconium tetrachloride and various dilithiated biscyclopentadienyl ligand systems, but no standard rules were able to be derived.

The known methods of preparing particular ansa-metallocenes in the meso form leave something to be desired both in respect of the economics and in respect of the applicability.

To be able to obtain a better assessment of the potential of ansa-metallocenes in the meso form, there is a need for various meso-metallocenes to be able to be obtained in a simple fashion.

It is an object of the present invention to discover a simple, economical and widely applicable process for preparing ansa-metallocenes in the meso form, which offers advantages both in terms of economics and in terms of the applicability.

We have found that this object is achieved by a process for the meso-selective preparation of ansa-metallocene complexes of the formula (I),

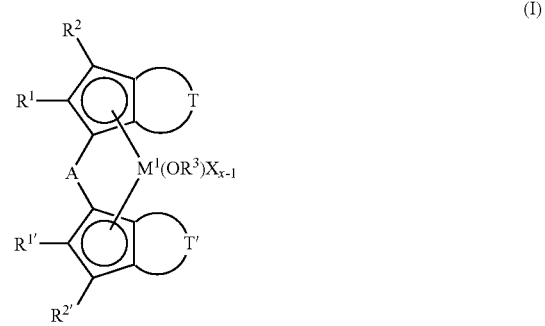

which comprises reacting a ligand starting compound of the formula (II)

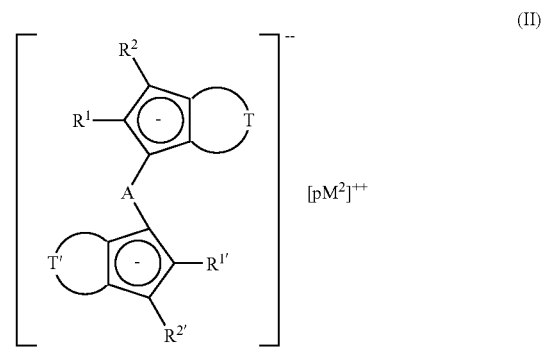

with a transition metal compound of the formula (III)

where
$R^1$, $R^{1'}$ are identical or different and are each hydrogen or an organic radical having from 1 to 40 carbon atoms,
$R^2$, $R^{2'}$ are identical or different and are each hydrogen or an organic radical having from 1 to 40 carbon atoms,
$R^3$ is a bulky organic radical which has at least 3 carbon atoms, is bound to the oxygen atom via a nonaromatic carbon or silicon atom and may be substituted by halogen atoms or further organic radicals having from 1 to 20 carbon atoms and may also contain heteroatoms selected from the group consisting of Si, N, P, O and S,
T, T' are identical or different and are each a divalent organic group which has from 1 to 40 carbon atoms and together with the cyclopentadienyl ring forms at least one further saturated or unsaturated, substituted or unsubstituted ring system having a ring size of from 5 to 12 atoms, where T and T' may contain the heteroatoms Si, Ge, N, P, As, Sb, O, S, Se or Te within the ring system fused to the cyclopentadienyl ring,
A is a bridge consisting of a divalent atom or a divalent group,
M' is an element of group 3, 4, 5 or 6 of the Periodic Table of the Elements or the lanthanides,
the radicals x are identical or different and are each an organic or inorganic radical which is able to be replaced by a cyclopentadienyl anion,
x is a natural number from 1 to 4,
$M^2$ is an alkali metal, an alkaline earth metal or a magnesium monohalide fragment, p is 1 in the case of doubly positively charged metal ions or 2 in the case of singly positively charged metal ions or metal ion fragments, LB is an uncharged Lewis base ligand, and y is a natural number from 0 to 6.

The radicals $R^1$ and $R^{1'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical which contains at least one heteroatom selected from the group consisting of the elements O, N, S, P and Se, in particular O, N and S, and may be substituted by further radicals $R^6$, where $R^6$ is an organic radical having from 1 to 20 carbon atoms, for example $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 18, preferably from 6 to 10, carbon atoms in the aryl radical, and a plurality of radicals $R^6$ can be identical or different.

Preference is given to $R^1$ and $R^{1'}$ being identical or different, preferably identical, and each being $C_1$-$C_{10}$-alkyl such as methyl, ethyl, n-propyl, isopropyl, n-butyl, i-butyl, s-butyl, t-butyl, n-pentyl, cyclopentyl, n-hexyl, cyclohexyl, n-heptyl or n-octyl, preferably methyl, ethyl or isopropyl, in particular methyl.

The radicals $R^2$ and $R^{2'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl each having from 1 to 10, preferably from 1 to 4, carbon atoms in the alkyl part and from 6 to 22, preferably from 6 to 10, carbon atoms in the aryl part, or a $C_2$-$C_{40}$-heteroaromatic radical which contains at least one heteroatom selected from the group consisting of the elements O, N, S, P and Se, in particular O, N and S, and may be substituted by further radicals $R^6$, as defined above, and a plurality of radicals $R^6$ can be identical or different. Preference is given to $R^2$ and $R^{2'}$ each being hydrogen.

The radical $R^3$ is a bulky organic radical which has at least 3 carbon atoms, preferably from 4 to 40 carbon atoms, is bound to the oxygen atom via a nonaromatic carbon or silicon atom, preferably a carbon atom, and may be substituted by halogen atoms or further organic radicals having from 1 to 20 carbon atoms and may also contain heteroatoms selected from the group consisting of Si, N, P, O and S, preferably N, O and S. A nonaromatic carbon or silicon atom is an atom of this type which is not located within an aromatic or heteroaromatic ring system, i.e. the oxygen atom of the $OR^3$ group is not bound directly to an aromatic or heteroaromatic radical. Examples of such bulky alkyl radicals are isopropyl, cyclohexyl, tert-butyl, 1-adamantyl, 2-adamantyl, triphenylmethyl, diphenylmethyl, (1R)-endo-(+)-1,3,3-trimethyl-2-norbornyl, trimethylsilyl, triphenylsilyl and dimethyl-tert-butylsilyl.

$R^3$ is preferably an alkyl radical which is branched in the α position and has from 4 to 40, preferably from 7 to 40, carbon atoms and may be substituted by halogen atoms such as fluorine, chlorine, bromine or iodine, in particular fluorine or chlorine, or organic radicals having from 1 to 10 carbon atoms. In this context, an alkyl radical which is branched in the α position is an alkyl radical whose linking α atom bears at least two directly bound atoms which are different from hydrogen and not more than one directly bound hydrogen atom.

$R^3$ is particularly preferably a bicyclic or polycyclic alkyl radical which has from 7 to 30 carbon atoms and may be substituted by one or more $C_1$-$C_4$-alkyl radicals.

T and T' are identical or different, preferably identical, and are each a divalent organic group which has from 1 to 40 carbon atoms and together with the cyclopentadienyl ring forms at least one further saturated or unsaturated, substituted or unsubstituted ring system having a ring size of from 5 to 12, in particular from 5 to 7, atoms, where T and T' may contain the heteroatoms Si, Ge, N, P, As, Sb, O, S, Se or Te, preferably Si, N, O or S, in particular S or N, within the ring system fused to the cyclopentadienyl ring.

Examples of preferred divalent organic groups T or T' are

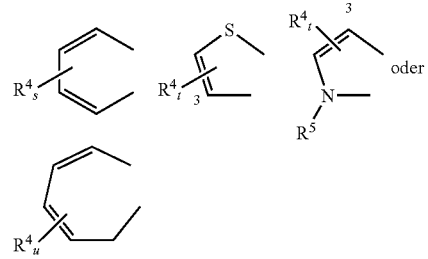

preferably

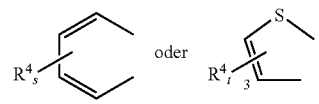

in particular

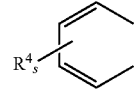

where the radicals $R^4$ are identical or different and are each an organic radical having from 1 to 40, preferably from 1 to 20, carbon atoms, for example cyclic, branched or unbranched $C_1$-$C_{20}$-, preferably $C_1$-$C_8$-alkyl radicals, $C_2$-$C_{20}$-, preferably $C_2$-$C_8$-alkenyl radicals, $C_6$-$C_{22}$-, preferably $C_6$-$C_{10}$-aryl radicals, alkylaryl or arylalkyl radicals each having from 1 to 10, preferably from 1 to 4, carbon atoms in the alkyl part and from 6 to 22, preferably from 6 to 10, carbon atoms in the aryl part, where the radicals may also be halogenated, or the radicals $R^4$ are substituted or unsubstituted, saturated or unsaturated, in particular aromatic, heterocyclic radicals which have from 2 to 40, in particular from 4 to 20, carbon atoms and contain at least one heteroatom which is preferably selected from the group consisting of the elements O, N, S and P, in particular O, N and S, or two adjacent radicals $R^4$ together with the atoms connecting them form a monocyclic or polycyclic, substituted or unsubstituted ring system which has from 1 to 40 carbon atoms and may also contain heteroatoms selected from the group consisting of the elements Si, Ge, N, P, O, S, Se and Te, in particular N or S, $R^5$ is hydrogen or is as defined for $R^4$, s is a natural number from 0 to 4, in particular from 0 to 3, t is a naturalenumber from 0 to 2, in particular 1 or 2, and u is a natural number from 0 to 6, in particular 1.

A is a bridge consisting of a divalent atom or a divalent group. Examples of A are:

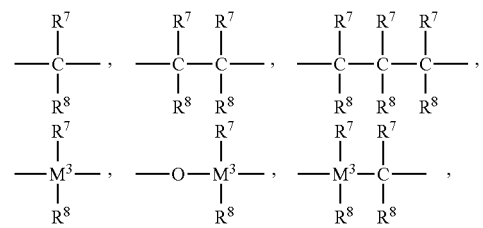

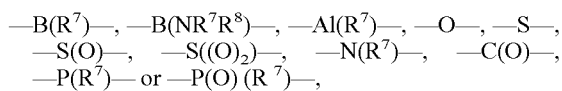

in particular

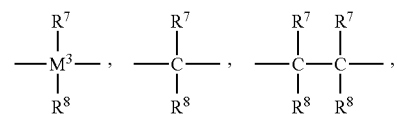

where $M^3$ is silicon, germanium or tin, preferably silicon or germanium, particularly preferably silicon, and $R^7$, $R^8$ and $R^9$ are identical or different and are each a hydrogen atom, a halogen atom, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_7$-$C_{15}$-alkylaryloxy group, a $C_2$-$C_{10}$-, preferably $C_2$-$C_4$-alkenyl group, a $C_7$-$C_{40}$-arylalkyl group, a $C_8$-$C_{40}$arylalkenyl group or a $C_7$-$C_{40}$-alkylaryl group or two adjacent radicals together with the atoms connecting them form a saturated or unsaturated ring having from 4 to 15 carbon atoms.

Preferred embodiments of A are the bridges: dimethylsilanediyl, methylphenylsilanediyl, diphenylsilanediyl, dimethylgermandiyl, ethylidene, 1-methylethylidene, 1,1-dimethylethylidene, 1,2-dimethylethylidene, 1,1,2,2-tetramethylethylidene, dimethylmethylidene, phenylmethylmethylidene or diphenylmethylidene, in particular dimethylsilanediyl, diphenylsilanediyl and ethylidene.

A is particularly preferably a substituted silylene group or a substituted or unsubstituted ethylene group, preferably a substituted silylene group such as dimethylsilanediyl, methylphenylsilanediyl, methyl-tert-butylsilanediyl or diphenylsilanediyl, in particular dimethylsilanediyl.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium or hafnium, particularly preferably zirconium or hafnium and very particularly preferably zirconium.

The radicals X are identical or different and are each an organic or inorganic radical which is able to be replaced by a cyclopentadienyl anion. Examples of X are halogen such as chlorine, bromine, iodine, in particular chlorine, organosulfonate groups such as trifluoromethanesulfonate (triflate) or mesylate. X is preferably halogen, in particular chlorine.

x is a natural number from 1 to 4 and usually corresponds to the oxidation number of $M^1$ minus 2. In the case of elements of group 4 of the Periodic Table of the Elements, x is preferably 2.

$M^2$ is an alkali metal such as Li, Na or K, an alkaline earth metal such as Mg or Ca, in particular Mg, or a magnesium monohalide fragment such as MgCl, MgBr or MgI. $M^2$ is preferably Li, Na, K, MgCl, MgBr, MgI or Mg, particularly preferably Li, K or Mg, in particular Li.

p is 1 for doubly positively charged metal ions or 2 for singly positively charged metal ions or metal ion fragments.

LB is an uncharged Lewis base ligand, preferably a linear, cyclic or branched oxygen-, sulfur, nitrogen- or phosphorus-containing, in particular oxygen- or nitrogen-containing, hydrocarbon such as an ether, polyether, thioether, amine, polyamine or phosphine. LB is preferably a cyclic or acyclic ether or diether, for example diethyl ether, dibutyl ether, tert-butyl methyl ether, anisole, dimethoxyethane (DME), tetrahydrofuran (THF) or dioxane. Particular preference is given to THF or DME.

y is a natural number from 0 to 6. In the case of elements of group 4 of the Periodic Table of the Elements, y is preferably 1 or 2.

Furthermore, the substituents according to the present invention are, unless restricted further, defined as follows:

The term "organic radical having from 1 to 40 carbon atoms" as used in the present context refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterecyclic radicals, $C_6$-$C_{40}$-aryl radicals, $C_2$-C40-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl (HOC($H_2$)—).

The term "alkyl" as used in the present context encompasses linear or singly or multiply branched saturated hydrocarbons which may also be cyclic. Preference is given to a $C_1$-$C_{18}$-alkyl group such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present context encompasses linear or singly or multiply branched hydrocarbons having at least one, if desired more than one, C-C double bonds which may be cumulated or alternating.

The term "saturated heterocyclic radical" as used in the present context refers, for example, to monocyclic or polycyclic, substituted or unsubstituted hydrocarbon radicals in which one or more carbon atoms, CH groups and/or $CH_2$ groups have been replaced by heteroatoms which are preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothienyl and the like, and also methyl-, ethyl-, propyl-, isopropyl- and tert-butyl-substituted derivatives thereof.

The term "aryl" as used in the present context refers, for example, to aromatic and fused or unfused polyaromatic hydrocarborn substituents which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl and 4-trifluoromethylphenyl.

The term "heteroaromatic radical" as used in the present context refers, for example, to aromatic hydrocarbon radicals in which one or more carbon atoms have been replaced by nitrogen, phosphorus, oxygen or sulfur atoms or combinations thereof. They may, like the aryl radicals, be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present context refers, for example, to aryl-containing substituents whose aryl radical is connected via an alkyl chain to the remainder of the molecule. Preferred examples are benzyl, substitutued benzyl, phenethyl, substituted phenethyl and the like.

The terms fluoroalkyl and fluoroaryl indicate that at least one hydrogen atom, preferably two or more and at most all hydrogen atoms, of the respective substituent have been replaced by fluorine atoms. Examples of fluorine-containing substituents which are preferred according to the present invention are trifluoromethyl, 2,2,2-trifluoroethyl, pentafluorophenyl, 4-trifluoromethylphenyl, 4-perfluoro-tert-butylphenyl and the like.

In a preferred embodiment of the process of the present invention, the metallocene complex of the formula (I) is converted into an ansa-metallocene complex of the formula (IV)

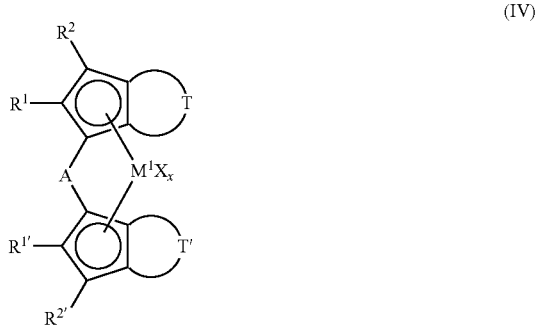

(IV)

where the variables and indices have the same meanings as in the formula (I), by reaction with suitable elimination reagents in a subsequent reaction step.

The present invention therefore also provides for the use of a metallocene complex of the formula (I) as intermediate for preparing ansa-metallocene complexes of the formula (IV).

Elimination reagents are known in principle. Examples of preferred elimination reagents are hydrogen halides, for example HCl, and aliphatic or aromatic carboxylic halides, for example acetyl chloride, acetyl bromide, phenylacetyl chloride, tert-butylacetyl chloride, and also organoaluminum halides, for example ethylaluminum dichloride, methylaluminum dichloride or dimethylaluminum chloride, and halogen-containing main group compounds such as $SiCl_4$, $SOCl_2$, $PCl_5$ or $AlCl_3$.

Particularly preferred elimination reagents are HCl, acetyl chloride, ethylaluminum dichloride and methylaluminum dichloride.

The elimination reaction is usually carried out in a temperature range from 0° C. to 110° C. To complete the reaction, it is usual to use at least stoichiometric amounts of the elimination reagent.

Excess elimination reagent generally does not interfere as long as it can be separated off from the target product without problems in the work-up.

Particular preference is given to a process for the meso-selective preparation of ansa-metallocene complexes of the formula (I) which optionally further comprises the subsequent reaction of these complexes to form ansa-metallocenes of the formula (IV)

in which $R^1$, $R^{1'}$ are identical or different and are each $C_1$-$C_{10}$-alkyl such as methyl, ethyl, isopropyl, tert-butyl, cyclohexyl or octyl, in particular methyl, $R^2$, $R^{2'}$ are each hydrogen, T, T' are identical or different and are each an unsubstituted 1,3-butadiene-1,4-diyl group or a 1,3-butadiene-1,4-diyl group substituted by from 1 to 4 radicals $R^4$, where $R^4$ can be identical or different and are organic radicals having from 1 to 40 carbon atoms, A is ethylene, substituted ethylene or substituted silylene, in particular substituted silylene such as dimethylsilanediyl, methylphenylsilanediyl, methyl-tert-butylsilanediyl or diphenylsilanediyl, in particular dimethylsilanediyl, and the variables $R^3$, $M^1$, X, $M^2$ and LB and also the indices x, p and y are as defined for the formula I.

Very particular preference is given to a process for the meso-selective preparation of ansa-metallocene complexes of the formula (I) or the formula (IV), as described above, in which $R^3$ is an alkyl radical which is branched in the α position and has from 4 to 40, preferably from 7 to 40, carbon atoms and may be substituted by halogen atoms such as fluorine, chlorine, bromine or iodine, in particular fluorine or chlorine, or by organic radicals having from 1 to 10 carbon atoms, with $R^3$ particularly preferably being a bicyclic or polycyclic alkyl radical which has from 7 to 30 carbon atoms and may be substituted by one or more $C_1$-$C_4$-alkyl radicals, $M^1$ is Ti, Zr or Hf, preferably Zr or Hf, in particular Zr, X is halogen, in particular chlorine, x is 2, LB is acyclic or acyclic ether or diether, in particular THF or DME, and y is 1 or 2.

In the process of the present invention, the salt-like ligand starting compounds of the formula (II) can either be used in isolated form or be prepared in-situ immediately before the reaction with the transition metal compound of the formula (III).

To synthesize the salt-like ligand starting compounds of the formula (II), the corresponding uncharged bridged biscyclopentadienyl compound is usually doubly deprotonated by means of a strong base. Strong bases which can be used are, for example, organometallic compounds or metal hydrides, preferably compounds containing an alkali metal or an alkaline earth metal. Preferred bases are organolithium or organomagnesium compounds such as methyllithium, n-butyllithium, sec-butyllithium, n-butyl-n-octylmagnesium or dibutylmagnesium.

The uncharged bridged biscyclopentadienyl compound to be deprotonated can also be used in isolated form or without isolation, prepared directly by the coupling reaction of two cyclopentadienyl anions with an appropriate bridging reagent, for example a diorganodichlorosilane such as dimethyldichlorosilane. A further possible way of preparing the uncharged biscyclopentadienyl compounds is stepwise construction. Here, for example, a cyclopentadienyl anion is firstly reacted with an appropriate bridging reagent, for example a diorganodichlorosilane such as dimethyldichlorosilane, to form a monochloromonocyclopentadienyldiorganosilane compound and the chlorine in this is subsequently replaced by a further cyclopentadienyl radical, which may be different from the first cyclopentadienyl radical, to obtain the desired uncharged bridged biscyclopentadienyl compound.

The synthesis of the cyclopentadienyl anions can in principle be carried out under the same conditions as the deprotonation of the uncharged bridged biscyclopentadienyl compound.

The double deprotonation of the uncharged bridged biscyclopentadienyl compound to form the ligand starting compound of the formula (II) is usually carried out at from −78° C. to 110° C., preferably from 0° C. to 80° C. and particularly preferably from 20° C. to 70° C.

Suitable inert solvents in which the deprotonation of the cyclopentadienyl derivatives by means of strong bases can be carried out are aliphatic or aromatic hydrocarbons such as benzene, toluene, xylene, mesitylene, ethylbenzene, cumene, decalin, tetralin, pentane, hexane, cyclohexane, heptane or ethers such as diethyl ether, di-n-butyl ether, tert-butyl methyl ether (MTBE), tetrahydrofuran (THF), 1,2-dimethoxyethane (DME), anisole, triglyme, dioxane and any mixtures of these substances. Preference is given to solvents or solvent mixtures in which the subsequent process of the present invention for preparing the metallocene complexes of the formula (I) can likewise be carried out directly.

The synthesis of the transition metal compounds of the formula (III) is in principle known from the literature. A possible way of preparing them is, for example, reaction of a transition metal compound $M^1X_{x+2}$ or $(LB)_yM^1X_{x+2}$ with a metal alkoxide $M^2(OR^3)$ in an inert solvent, where $M^{2t}$ and $M^2$ and the other variables are as defined for the formula (I).

In the process of the present invention, the reaction of the ligand starting compound of the formula (II) with the transition metal compound of the formula (III) can be carried out in an inert solvent or solvent mixture at from −78° C. to 150° C., in particular from 0° C. to 110° C. The inert solvents or solvent mixtures which can be used are preferably the same ones in which the synthesis of the ligand starting compound of the formula (II) has been carried out. The reaction times are usually at least 10 minutes, generally from 1 to 8 hours.

The present invention therefore also provides for the use of a transition metal compound of the formula (III)

$$(LB)_yM^1(OR^3)X_{x+1} \qquad (III)$$

for the preparation of ansa-metallocene complexes, in particular for the meso-selective preparation of ansa-metallocene complexes of the formula (I) or for the preparation of ansa-metallocene complexes of the formula (IV) by the process of the present invention, where the variables and indices are as described above.

The present invention further provides transition metal compounds of the formula (III)

$$(LB)_yM^1(OR^3)X_{x+1} \qquad (III)$$

where the variables and indices are as described above.

Particular preference is given to compounds of the formula (III) in which $R^3$ is an alkyl radical which is branched in the α position and has from 4 to 40, in particular from 7 to 40, carbon atoms and may be substituted by halogen atoms or organic radicals having from 1 to 10 carbon atoms, in particular compounds in which $R^3$ is a bicyclic or polycyclic alkyl radical having from 7 to 30 carbon atoms and optionally bearing one or more $C_1$-$C_4$-alkyl radicals as substituents and in which $M^1$ is Ti, Zr or Hf, in particular Zr or Hf, and in which X is halogen, in particular chlorine, x is 2, LB is a cyclic or acyclic ether or diether and y is 1 or 2.

In the process of the present invention, it is possible for not only the desired meso compounds of the formula (I) but also the corresponding rac compounds to be formed, where the terms meso and rac refer to the spatial arrangement of the two cyclopentadienyl ring systems relative to one another. For example, in cases in which the two cyclopentadienyl radicals on the bridge are not identical, there is no meso form having $C_s$ symmetry or rac form having $C_2$ symmetry, but instead there are only diastereomeric compounds having $C_1$ symmetry. These various diastereomeric metallocene compounds which differ from one another in the spatial arrangement of the different substituents behave, when used as catalyst components in the polymerization of propylene, like the $C_s$-symmetric meso isomer (atactic polypropylene) or like the $C_2$-symmetric rac isomer (isotactic polypropylene) simply on the basis of the spatial arrangement of the two cyclopentadienyl ligands relative to one another and can thus be referred to as either a pseudo-rac form or a pseudo-meso form.

meso or pseudo-meso (I)

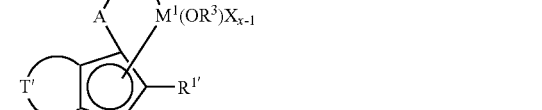

rac or pseudo-rac (Ia)

In the following, meso and pseudo-meso form and rac and pseudo-rac form are distinguished simply as rac and meso forms.

Furthermore, the meso selectivity=(proportion of meso−proportion of rac)/(proportion of rac+proportion of meso) in the process of the present invention is greater than zero, preferably greater than 0.5.

The salts of the formulae $M^2X$ or $M^2X_2$, for example lithium chloride or magnesium chloride, which are obtained as further reaction product in the process of the present invention for preparing meso ansa-metallocenes of the formula (I) can be separated off from the metallocene by known methods. For example, a salt such as lithium chloride can be precipitated by means of a suitable solvent in which the metallocene is, however, soluble, so that the solid lithium chloride is separated off from the dissolved metallocene by means of a filtration step. The metallocene can also be separated off from the salt by extraction with such a solvent. If filtration steps are employed, use can also be made of filter aids such as kieselguhr. Organic solvents which are suitable for such a filtration or extraction step are, in particular, organic aprotic, oxygen-free solvents such as toluene, ethylbenzene, xylenes and methylene chloride. If appropriate, the solvent constituents in which the salt is at least partially soluble are largely removed before the above-described removal of the salt. For example, lithium chloride is appreciably soluble in tetrahydrofuran. For this reason, an alternative is to remove the salts of the formulae $M^2X$ and $M^2X_2$ with the aid of a solvent or solvent mixture in which they are readily soluble while the metallocene complex is sparingly soluble therein.

The ansa-metallocene complexes of the formula (I) prepared by the process of the present invention are used, together with suitable cocatalysts and, if appropriate, suitable support materials, as constituents of a catalyst system for the polymerization of olefins.

The present invention further provides ansa-metallocene complexes of the formula (I) as are obtainable by the process of the present invention and also the use of an ansa-metallocene complex of the formula (I) prepared by a process as claimed in claim 1 as constituent of a catalyst system for the polymerization of olefins.

Preference is given to ansa-metallocene complexes of the formula (I) as described above in which $R^3$ is a bicyclic or polycyclic alkyl radical which has from 7 to 30 carbon atoms and may bear one or more $C_1$-$C_4$-alkyl radicals as substituents, $M^1$ is Ti, Zr or Hf, in particular Zr or Hf, X is halogen, in particular chlorine, and x is 2.

Preference is given to metallocene mixtures which are obtainable directly by the process of the present invention and comprise more than 50 mol % of metallocenes of the formula (I) and less than 50 mol % of metallocenes of the formula (Ia), based on the total amount of metallocene compounds. Particular preference is given to mixtures which comprise more than 75 mol % of metallocenes of the formula (I) and less than 25 mol % of metallocenes of the formula (Ia).

The invention is illustrated by the following nonrestrictive examples:

EXAMPLES

General Procedures

Synthesis and handling of the organometallic compounds was carried out in the absence of air and moisture under argon (glove box and Schlenk technique). All solvents used were purged with argon and dried over molecular sieves before use. NMR spectra of organic and organometallic compounds were recorded at room temperature on a Varian Unity-300 NMR spectrometer. The chemical shifts are reported relative to $SiMe_4$.

1. Synthesis of meso-dimethylsilanediylbis(2-methylindenyl)zirconium dichloride via intermediate isolation of meso-dimethylsilanediylbis(2-methylindenyl)zirconium monochloride 1-adamantoxide 1a Synthesis of $ZrCl_4(THF)_2$ Under protective gas, 15.2 g of zirconium tetrachloride were suspended in 80 g of dry toluene. The suspension was cooled in an ice bath and 12 g of tetrahydrofuran (THF) were added slowly. The colorless suspension was subsequently stirred at room temperature for a further one hour.

1b Synthesis of lithium 1-adamantoxide

A solution of 9.6 g of 1-adamantanol in 80 g of toluene and 12 g of THF was cooled in an ice bath and 21.2 g of a solution of n-butyllithium (20% by weight in toluene) were added dropwise over a period of half an hour. The reaction mixture was subsequently stirred at room temperature for a further hour.

1c Synthesis of $(THF)_2Cl_3Zr(1$-adamantoxide)

The solution of lithium 1-adamantoxide prepared in example 1b was added dropwise at room, temperature to the suspension of the zirconium tetrachloride-THF complex prepared in example 1a over a period of 20 minutes. The reaction mixture was stirred at room temperature for a further 2 hours.

1d Synthesis of $Li_2$[dimethylsilanediylbis(2-methylindenyl)]

42 g of a solution of n-butyllithium (20% by weight in toluene) were added at 0-4° C. to a solution of 20 g of dimethylbis(2-methylindenyl)silane (63.30 mmol) in 132 g of toluene and 12 g of THF over a period of 30 minutes. A yellowish beige suspension was formed and this was stirred at room temperature for a further 1.5 hours.

1e Synthesis and isolation of meso-dimethylsilanediylbis(2-methylindenyl)zirconium monochloride 1 -adamantoxide (1e)

The suspension of $(THF)_2Cl_3Zr(1$-adamantoxide) prepared in example 1c was added at room temperature to the suspension of $Li_2$[dimethylsilanediylbis(2-methylindenyl)] prepared in example 1d, resulting in immediate formation of a yellow suspension. The suspension was stirred at room temperature for a further 2.5 hours and subsequently filtered through a G4 frif. The filtercake was extracted three times with 200 g each time of toluene. The combined filtrates were concentrated under reduced pressure to 12% of the initial mass and allowed to stand at −20° C. for 16 hours. The yellow precipitate formed was filtered off, washed with 15 ml of toluene and dried under reduced pressure. This gave 6.16 g of (1e) as a yellow powder. The orange filtercake which remained after the toluene extraction was extracted with 200 g of dichloromethane. Removal of the solvent under reduced pressure once again gave a yellow powder which was washed with 30 g of heptane and subsequently dried in an oil pump vacuum. A further 11.36 g of complex (1e) were obtained. Overall, the complex (1e) was-obtained in a yield of 46.7% (17.52 g) in the form of a yellow powder.

$^1$H-NMR ($CD_2Cl_2$): 7.72 (dd, J=8.7 Hz and 1.0 Hz, 2H, aromatic), 7.22-7.19 (m, 2H, aromatic), 7.00-6.96 (m, 2H, aromatic), 6.65-6.61 (m, 2H, aromatic), 6.25 (s, 1H, Cp), 2.52 (s, 6H, 2×$CH_3$-Cp), 2.15-2.12 (m, 3H, adamantyl), 1.80-1.79 (m, 6H, adamantyl), 1.50-1.48 (m, 6H, adamantyl), 1.37 (s, 3H, $CH_3Si$), 1.20 (s, 3H, $CH_3Si$).

1. Synthesis of meso-dimethylsilanediylbis(2-methylindenyl)zirconium dichloride (1)

2 g of acetyl chloride were added to a suspension of 10 g of the complex (1e) prepared in example 1e in 100 ml of n-heptane. The reaction mixture was stirred at 40° C. for 5 hours. The orange suspension was filtered through a G3 frit, the filtercake was washed with 30 g of n-heptane and 20 g of toluene and dried under reduced pressure. This gave 5.12 g of the compound (1) as an orange powder (64% yield based on (1e)).

$^1$H-NMR (CD$_2$Cl$_2$: 7.67 (dd, J=8.8 Hz and 0.9Hz, 2H, aromatic), 7.38-7.36 (m, 2H, aromatic), 7.11-7.07 (m, 2H, aromatic), 6.77-6.73 (m, 2H, aromatic), 6.65 (s, 1H, Cp), 2.44 (s, 6H, 2×CH$_3$-Cp), 1.43 (s, 3H, CH$_3$Si), 1.23 (s, 3H, CH$_3$Si).

2. Single-vessel synthesis of meso-enriched dimethylsilanediylbis(2-methylindenyl)zirconium dichloride (1) without intermediate isolation of dimethylsilanediylbis(2-methylindenyl)zirconium monochloro 1-adamantoxide A suspension of (THF)$_2$Cl$_3$Zr(1-adamantoxide) which had been prepared in the same amount and in the same way as in example 1c was added to a suspension of Li$_2$[dimethylsilanediylbis(2-methylindenyl)] which had been prepared as in example 1d and the mixture was stirred at room temperature for 2.5 hours. The yellow suspension was filtered through a G4 glass frit filter and the filtercake was extracted three times with 200 g each time of toluene. The filtrate was evaporated to 50% of its original weight. 4.98 g of acetyl chloride were added to the solution and the reaction mixture was stirred at 40° C. for 3 hours. The reaction solution was concentrated to 10% of its initial mass. The precipitate formed was filtered off with the aid of a G3 glass frit filter, washed with 10 g of toluene and dried under reduced pressure. This gave 4 g of the compound (1) in the form of an orange powder (14% yield), with the rac/meso ratio as determined by $^1$H-NMR being 1:4.

3. Single-vessel synthesis of meso-enriched dimethylsilanediylbis(2-methylindenyl)zirconium dichloride (1) without intermediate isolation of meso-enriched dimethylsilanediylbis(2-methylindenyl)zirconium monochloride endo-(−)-fenchoxide The experiment was carried out in a manner analogous to example 2. ZrCl$_4$(THF)$_2$ was prepared in the same amount as in example 1a and combined with a solution of lithium endo-(−)-fenchoxide which had been prepared from 9.76 g of endo-(−)-fenchol and 21.2 g of a solution of n-butyllithium (20% by weight in toluene) by a method analogous to example 1b, giving a suspension of (THF)$_2$Cl$_3$Zr(fenchoxide). This suspension was added to a suspension of Li$_2$[dimethylsilanediylbis(2-methylindenyl)] which had been prepared as described in example 1d from 20 g of dimethylbis(2-methylindenyl) silane (63.30 mmol). This resulted in immediate formation of a yellow suspension which was stirred at room temperature for 1.5 hours. The yellow suspension was filtered through a G4 glass frit filter and the filtercake was extracted 3 times with 200 g each time of toluene. The filtrate was evaporated to 12% of its initial mass. Some yellow crystals were able to be isolated, and these were examined by NMR spectroscopy and found to be dimethylsilanediylbis(2-methylindenyl)zirconium monochloride endo-(−)-fenchoxide.

$^1$H-NMR (CD$_2$Cl$_2$: 7.66-7.63 (m,2H, aromatic), 7.27-7.15 (2dd, 2H, aromatic), 7.05-6.98 (m, 2H, aromatic), 6.69-6.65 (m, 2H, aromatic), 6.58 and 6.36 (2s, 2H, 2×Cp), 3.91 (s, 1H, fenchyl), 2.53 and 2.49 (2s, 6H, 2×CH$_3$-Cp), 1.36, 1.20 and 1.18 (3s, 9H, CH$_3$-fenchyl), 1.03 (s, 3H, CH$_3$Si), 0.92 (s, 3H, CH$_3$Si), 1.69-1.30, 1.10-1.04, 0.98 and 0.85-0.77 (m, H, fenchyl).

4.97 g of acetyl chloride were added to the partly evaporated solution and the reaction mixture was stirred at 40° C. for one hour. The precipitate was filtered off with the aid of a G3 glass frit filter, washed with 40 g of n-heptane and dried under reduced pressure. This gave 4.51 g of the compound (1) in the form of an orange powder (14% yield), with the rac/meso ratio as determined by $^1$H-NMR being 1:6.

We claim:

1. A process for meso-selective preparation of ansa-metallocene complexes of formula (I):

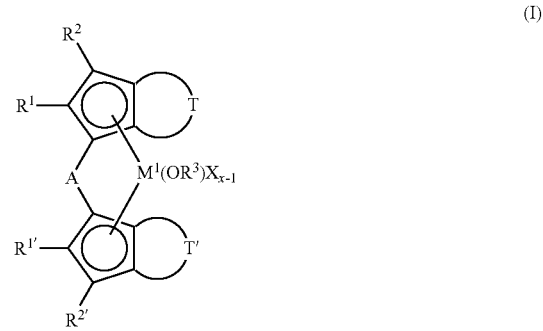

which comprises reacting a ligand starting compound of formula (II):

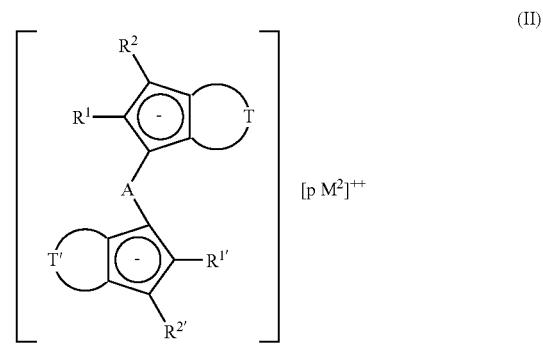

with a transition metal compound of formula (III):

$(LB)_yM^1(OR^3)X_{x+1}$      (III)

where $R^1$, $R^{1'}$ are identical or different and are each hydrogen or an organic radical having from 1 to 40 carbon atoms;

$R^2$, $R^{2'}$ are identical or different and are each hydrogen or an organic radical having from 1 to 40 carbon atoms;

$R^3$ is a bulky organic radical comprising at least 3 carbon atoms, and is bound to the oxygen atom via a nonaromatic carbon or silicon atom, and may be substituted by halogen atoms or further organic radicals comprising from 1 to 20 carbon atoms, and optionally comprise at least one heteroatom selected from the group consisting of Si, N, P, O and S;

T, T' are identical or different and are each a divalent organic group comprising from 1 to 40 carbon atoms, and together with the cyclopentadienyl rings form at least one further saturated or unsaturated, substituted or unsubstituted ring system comprising from 5 to 12 atoms, where T and T' optionally comprises at least one heteroatom selected from Si, Ge, N, P, As, Sb, O, S, Se or Te;

A is a bridge consisting of a divalent atom or a divalent group;

$M^1$ is at least one lanthanide or an element of group 3, 4, 5 or 6 of the Periodic Table of Elements;

X are identical or different and are each an organic or inorganic radical which is able to be replaced by a cyclopentadienyl anion;

x is a natural number from 1 to 4;

$M^2$ is an alkali metal, an alkaline earth metal, or a magnesium monohalide fragment;

p is 1 when $M^2$ is a doubly positively charged metal ion, or 2 when $M^2$ is a singly positively charged metal ion or metal ion fragment;

LB is an uncharged Lewis base ligand; and y is a natural number from 0 to 6.

2. The process as claimed in claim 1, wherein an ansa-metallocene complex of formula (I) is converted into an ansa-metallocene complex of formula (IV):

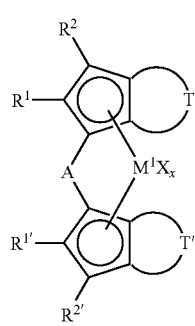

(IV)

where $R^1$, $R^{1'}$ are identical or different and are each hydrogen or an organic radical having from 1 to 40 carbon atoms;

$R^2$, $R^{2'}$ are identical or different and are each hydrogen or an organic radical having from 1 to 40 carbon atoms;

T, T' are identical or different and are each a divalent organic group comprising from 1 to 40 carbon atoms, and together with the cyclopentadienyl rings form at least one further saturated or unsaturated, substituted or unsubstituted ring system comprising from 5 to 12 atoms, where T and T' optionally comprises at least one heteroatom selected from Si, Ge, N, P, As, Sb, O, S, Se or Te;

A is a bridge consisting of a divalent atom or a divalent group;

$M^1$ is at least one lanthanide or an element of group 3, 4, 5 or 6 of the Periodic Table of Elements;

X are identical or different and are each an organic or inorganic radical which is able to be replaced by a cyclopentadienyl anion; and x is a natural number from 1 to 4;

comprising reacting the ansa-metallocene complexes of formula (I) with at least one suitable elimination reagent in a subsequent reaction step.

3. The process as claimed in claim 1, wherein $R^1$, $R^{1'}$ are identical or different and are each a $C_1$-$C_{10}$-alkyl;

$R^2$, $R^{2'}$ are each hydrogen;

T, T' are identical or different and are each an unsubstituted 1,3-butadiene-1,4-diyl group or a 1,3-butadiene-1,4-diyl group substituted with from 1 to 4 $R^4$ radicals, where $R^4$ can be identical or different and are organic radicals having from 1 to 40 carbon atoms; and A is ethylene, substituted ethylene or substituted silylene.

4. The process as claimed in claim 2, wherein $R^1$, $R^{1'}$ are identical or different and are each a $C_1$-$C_{10}$-alkyl;

$R^2$, $R^{2'}$ are each hydrogen;

T, T' are identical or different and are each an unsubstituted 1,3-butadiene-1,4-diyl group or a 1,3-butadiene-1,4-diyl group substituted with from 1 to 4 $R^4$ radicals, where $R^4$ can be identical or different and are organic radicals having from 1 to 40 carbon atoms; and A is ethylene, substituted ethylene or substituted silylene.

5. The process as claimed in claim 1, wherein $R^3$ is an alkyl radical branched in an α position, and comprises from 4 to 40 carbon atoms, and is optionally substituted by at least one halogen atom or organic radical comprising from 1 to 10 carbon atoms;

$M^1$ is Ti, Zr or Hf;

X is halogen;

x is 2;

LB is a cyclic or acyclic ether or diether; and y is 1 or 2.

6. The process as claimed in claim 2, wherein $R^3$ is an alkyl radical branched in an α position, and comprises from 4 to 40 carbon atoms, and is optionally substituted by at least one halogen atom or organic radical comprising from 1 to 10 carbon atoms;

$M^1$ is Ti, Zr or Hf;

X is halogen;

x is 2;

LB is a cyclic or acyclic ether or diether; and y is 1 or 2.

7. The process as claimed in claim 1, wherein $M^2$ is Li, Na, K, MgCl, MgBr, MgI or Mg.

8. The process as claimed in claim 2, wherein $M^2$ is Li, Na, K, MgCl, MgBr, MgI or Mg.

9. A method for preparing ansa-metallocene complexes comprising reacting a metallocene complex with a transition metal compound of formula (III):

$$(LB)_y M^1(OR^3)X_{X+1} \quad \text{(III)}.$$

10. A transition metal compound of the formula (III):

$$(LB)_y M^1(OR^3)X_{X+1} \quad \text{(III)}$$

where $R^3$ is a bulky organic radical comprising at least 3 carbon atoms, and is bound to the oxygen atom via a nonaromatic carbon or silicon atom, and may be substituted by halogen atoms or further organic radicals comprising from 1 to 20 carbon atoms, and optionally comprise at least one heteroatom selected from the group consisting of Si, N, P, O and S;

$M^1$ is at least one lanthanide or an element of group 3, 4, 5 or 6 of the Periodic Table of Elements;

X are identical or different and are each an organic or inorganic radical which is able to be replaced by a cyclopentadienyl anion;

x is a natural number from 1 to 4;

LB is an uncharged Lewis base ligand; and y is a natural number from 0 to 6.

11. A method for preparing ansa-metallocene complexes of formula (IV) as set forth in claim 2 comprising reacting a metallocene complex of formula (I):

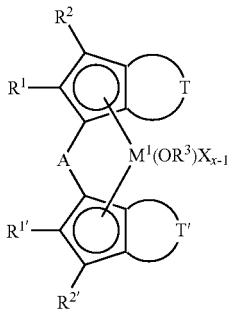

where
- $R^1$, $R^{1'}$ are identical or different and are each hydrogen or an organic radical having from 1 to 40 carbon atoms;
- $R^2$, $R^{2'}$ are identical or different and are each hydrogen or an organic radical having from 1 to 40 carbon atoms;
- $R^3$ is a bulky organic radical comprising at least 3 carbon atoms, and is bound to the oxygen atom via a nonaromatic carbon or silicon atom, and may be substituted by halogen atoms or further organic radicals comprising from 1 to 20 carbon atoms, and optionally comprise at least one heteroatom selected from the group consisting of Si, N, P, O and S;
- T, T' are identical or different and are each a divalent organic group comprising from 1 to 40 carbon atoms, and together with the cyclopentadienyl rings form at least one further saturated or unsaturated, substituted or unsubstituted ring system comprising from 5 to 12 atoms, where T and T' optionally comprises at least one heteroatom selected from Si, Ge, N, P, As, Sb, O, S, Se or Te;
- A is a bridge consisting of a divalent atom or a divalent group;
- $M^1$ is at least one lanthanide or an element of group 3, 4, 5 or 6 of the Periodic Table of Elements;
- X are identical or different and are each an organic or inorganic radical which is able to be replaced by a cyclopentadienyl anion; and
- x is a natural number from 1 to 4;

with a transition metal compound.

12. An ansa-metallocene complex of formula (I):

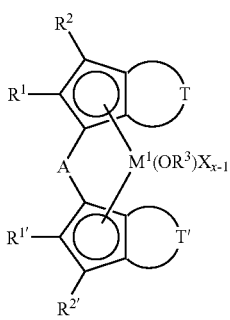

where
- $R^1$, $R^{1'}$ are identical or different and are each hydrogen or an organic radical having from 1 to 40 carbon atoms;
- $R^2$, $R^{2'}$ are identical or different and are each hydrogen or an organic radical having from 1 to 40 carbon atoms;
- T, T' are identical or different and are each a divalent organic group comprising from 1 to 40 carbon atoms, and together with the cyclopentadienyl rings form at least one further saturated or unsaturated, substituted or unsubstituted ring system comprising from 5 to 12 atoms, where T and T' optionally comprises at least one heteroatom selected from Si, Ge, N, P, As, Sb, O, S, Se or Te;
- A is a bridge consisting of a divalent atom or a divalent group;
- $R^3$ is an alkyl radical branched in an α position, and comprises from 4 to 40 carbon atoms, and is optionally substituted by at least one halogen atom or organic radical comprising from 1 to 10 carbon atoms;
- $M^1$ is Ti, Zr or Hf;
- X is halogen; and
- x is 2.

13. A constituent of a catalyst system for polymerizing at least one olefin comprising an ansa-metallocene complex of formula (I):

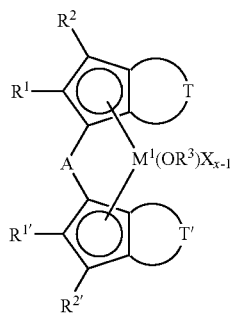

- $R^1$, $R^{1'}$ are identical or different and are each hydrogen or an organic radical having from 1 to 40 carbon atoms;
- $R^2$, $R^{2'}$ are identical or different and are each hydrogen or an organic radical having from 1 to 40 carbon atoms;
- $R^3$ is an alkyl radical branched in an α position, and comprises from 4 to 40 carbon atoms, and is optionally substituted by at least one halogen atom or organic radical comprising from 1 to 10 carbon atoms;
- T, T' are identical or different and are each a divalent organic group comprising from 1 to 40 carbon atoms, and together with the cyclopentadienyl rings form at least one further saturated or unsaturated, substituted or unsubstituted ring system comprising from 5 to 12 atoms, where T and T' optionally comprises at least one heteroatom selected from Si, Ge, N, P, As, Sb, O, S, Se or Te;
- A is a bridge consisting of a divalent atom or a divalent group;
- $M^1$ is at least one lanthanide or an element of group 3, 4, 5 or 6 of the Periodic Table of Elements;
- X are identical or different and are each an organic or inorganic radical which is able to be replaced by a cyclopentadienyl anion; and
- x is a natural number from 1 to 4.

* * * * *